(12) United States Patent
Smestad

(10) Patent No.: US 6,429,438 B1
(45) Date of Patent: Aug. 6, 2002

(54) ULTRAVIOLET LIGHT DETECTOR FOR LIQUID DISINFECTION UNIT

(75) Inventor: Greg P. Smestad, Monterey, CA (US)

(73) Assignee: WaterHealth International, Inc., Napa, CA (US)

( * ) Notice: Subject to any disclaimer, the term of this patent is extended or adjusted under 35 U.S.C. 154(b) by 0 days.

(21) Appl. No.: 09/351,964

(22) Filed: Jul. 12, 1999

(51) Int. Cl.[7] ............................................. G01N 21/01
(52) U.S. Cl. ..................................... 250/373; 250/431
(58) Field of Search ................................. 250/373, 431, 250/432, 436, 435, 455.11; 422/82.06

(56) References Cited

U.S. PATENT DOCUMENTS

| | | |
|---|---|---|
| 3,491,234 A | 1/1970 | Wiltrout |
| 3,710,111 A | 1/1973 | Collura |
| 4,201,916 A | 5/1980 | Ellner |
| 4,255,383 A * | 3/1981 | Schenck ...................... 422/24 |
| 4,272,679 A | 6/1981 | Blades |
| 4,304,996 A | 12/1981 | Blades |
| 4,317,041 A * | 2/1982 | Schenck ...................... 250/435 |
| 4,403,826 A | 9/1983 | Presby |
| 4,622,465 A | 11/1986 | Harig et al. |
| 4,629,896 A | 12/1986 | Bridgen |
| 4,742,231 A | 5/1988 | Bridgen |
| RE34,513 E | 1/1994 | Ellner |
| 5,401,394 A | 3/1995 | Markham |
| 5,420,432 A | 5/1995 | Manook et al. |
| 5,660,719 A | 8/1997 | Kurtz et al. |
| 5,923,039 A | 7/1999 | Jablonski et al. |
| 6,201,234 B1 * | 3/2001 | Chow et al. .......... 250/214 LS |

FOREIGN PATENT DOCUMENTS

| | | |
|---|---|---|
| EP | 0 059 140 A1 | 1/1982 |
| JP | 55-62357 | 10/1980 |

* cited by examiner

Primary Examiner—Constantine Hannaher
Assistant Examiner—Otilia Gabor

(57) ABSTRACT

An ultraviolet light detector for detecting levels of ultraviolet light in a liquid disinfection unit comprises two solid state silicon photodetectors. A first photodetector generates a photo-induced current proportional to the amount of visible, infra-red, and ultraviolet light emitted. A second photodetector generates a photo-induced current proportional to the amount of visible and infrared light emitted. The photodetectors are electrically connected in reverse parallel, generation an output current equal to the difference between the photo-induced currents of the photodetectors. The output current is thus proportional to the UV light intensity. The output current may be converted into a voltage, which may be monitored to ensure that the ultraviolet light intensity is sufficient for complete disinfection of the liquid. An electronic control system may be provided so that the output voltage controls a solenoid valve and/or an alarm in the disinfection unit. In particular, the solenoid valve is configured to control the liquid flow through the disinfection unit, and the alarm may be activated to alert system attendants.

14 Claims, 3 Drawing Sheets

ULTRAVIOLET LIGHT DETECTOR FOR LIQUID DISINFECTION UNIT

BACKGROUND OF THE INVENTION

1. Field of the Invention

The present invention generally relates to the utilization of ultraviolet (UV) light for the disinfection of water and other liquids, and specifically to the incorporation of a UV light detection system in a water disinfection unit.

2. Description of the Related Art

It has long been known to disinfect drinking water and other liquids by exposure to UV light. In fact, the first devices for doing so ("UV water disinfection units" or, alternatively, "UV water disinfectors") were developed in the early nineteen hundreds. Unfortunately, these early systems proved to be unreliable, impractical, and expensive, and were rapidly displaced by more attractive approaches, such as chlorination. However, UV technology has matured considerably since then and has become less expensive and more reliable. Also, health concerns about standard chlorine disinfection have accelerated the increasing popularity of UV water disinfection, particularly in Europe. By 1990, approximately 2000 municipal water treatment plants in Europe were using UV disinfection systems.

Most modern UV water disinfectors employ a construction wherein water is disinfected as it flows under a UV lamp. An exemplary device for cost-efficient, small-scale use is disclosed in U.S. Pat. No. 5,780,860 to Gadgil et al. Gadgil et al. teaches a highly effective, practical, and maintenance-free UV disinfection system, utilizing gravity-driven liquid delivery and treatment with a UV lamp.

A major concern with use of UV water disinfectors is the potential risk of output water that is not completely disinfected. Particularly in developing countries, many lives are lost annually due to the consumption of infected drinking water. Successful disinfection depends upon the intensity of the UV light, the turbidity and flowrate of the water as it passes underneath the UV lamp. If the UV light intensity is too low, the water will not receive enough UV energy for complete disinfection. Similarly, if the flowrate is too high, the water will not absorb enough UV energy as it passes under the lamp. Thus, there must be a balancing of the UV light intensity and the water flowrate. For a given system, if the UV light intensity is decreased, then so must be the flowrate. Conversely, if the flowrate is increased, then so must be the UV light intensity.

It is beneficial to include safety features in UV water disinfectors to prevent the delivery of water that is not successfully disinfected. For example, the system of Gadgil et al. illustrates the use of a solenoid valve electronically wired to close automatically and discontinue the flow of water to the UV lamp region if there is a stoppage of power to the UV lamp. In other words, the solenoid valve will shut off the entire system if there is a power outage or if the lamp bulb fuses. This feature is particularly advantageous for UV water disinfectors used in developing countries, where power outages are more frequent.

Another desirable safety feature is the utilization of UV light sensors to measure and monitor the intensity of the UV light exposed to the water. For any desired water flowrate, the UV light intensity received by the water can be readily determined by using fundamental principles of physics and mathematics. For successful disinfection, the UV light intensity must be maintained above a minimal level relative to the turbidity and flowrate. The sensors are provided to notify the system whenever the intensity drops dangerously close to the minimum intensity, which might occur if the power source to the UV lamp provides a fluctuating load. Typically, the system is designed to shut off in such a case, by utilizing some means for stopping the flow of water through the system, such as a solenoid valve as taught by Gadgil.

The turbidity of the water also affects the required level of UV light intensity for safe disinfection. For cloudy input water, a higher UV light intensity is required for complete disinfection. This is because, in more turbulent flows, the UV light is absorbed over a shorter distance.

Sensors used in UV water disinfectors are typically vacuum photodiodes constructed to be sensitive to UV light. This sensor includes two electrodes separated by a vacuum chamber, commonly enclosed within a quartz envelope. UV light striking the light-sensitive material causes electrons to shoot through the vacuum and generate an electric current directly proportional to the UV light intensity. The electrons are accelerated through the vacuum by application of an electric field between the electrodes. Using well known methods, this current signal is normally converted to a voltage output signal to indicate UV light intensity.

Unfortunately, the vacuum photodiode entails several disadvantages, particularly in the context of UV disinfection. One disadvantage is that the vacuum chamber and separated electrodes result in a relatively large size and high cost. Another disadvantage is that this sensor is relatively expensive, costing within the range of $50–$100. Another disadvantage is that the quartz envelope is very delicate and must be protectively encased, most commonly in epoxy and metal. This further adds to the cost of the sensor and, consequently, of the entire UV disinfection system. Furthermore, the delicateness of the vacuum photodiode results in a limited lifespan, normally less than five years. This necessitates frequent replacement and further adds to the operational costs. Another disadvantage of the vacuum photodiode is that it is less sensitive to fluctuations in UV light intensity. This results in relatively imprecise measurements thereof and thus adds to the uncertainty of the entire disinfection process.

Thus, there is a need for a more optically and mechanically stable, longer lasting, and less expensive method of sensing the amount of UV light intensity exposed to the water flowing through a UV water disinfector.

SUMMARY OF THE INVENTION

Accordingly, it is a principle object and advantage of the present invention to overcome some or all of these limitations and to provide an improved UV light sensor for a UV liquid disinfector.

In accordance with one aspect of the invention, an ultraviolet light detector is provided for detecting a level of ultraviolet light exposed to a liquid flowing within an ultraviolet liquid disinfection unit. The detector includes a first photodetector and a second photodetector. The first photodetector is configured to generate a first electric signal proportional to a level of a first spectrum of light, including ultraviolet light. The second photodetector is configured to generate a second electric signal proportional to a level of a second spectrum light, substantially including the first spectrum except for a range of ultraviolet light. The first and second electric signal are connected to generate an output electric signal that is equal to the difference between them, so that the output electric signal is proportional to a level of the range of ultraviolet light. In the illustrated embodiment, the output electric current is converted to a voltage and/or used to control various elements within the disinfection unit, such as an alarm and/or a solenoid valve configured to shut off the system.

In accordance with another aspect of the invention, a method is provided for detecting the amount of ultraviolet light in an ultraviolet liquid disinfection unit. According to this method, a first photo-induced electric current is generated. This current is proportional to the amount of a first spectrum of light exposed to liquid within the unit, including a range of ultraviolet light. A second photo-induced electric current is also generated. This current is proportional to the amount of a second spectrum of light exposed to the liquid. The first and second photo-induced electric currents are connected together to generate an output electric current proportional to the amount of the range of ultraviolet light exposed to the liquid.

In accordance with another embodiment of the invention, an ultraviolet disinfection unit is disclosed. The unit includes a liquid flow path and an ultraviolet lamp positioned to irradiate liquid within the flow path. A first photo detector is configured to generate a first electric signal, which is indicative of an amount of a first spectrum of light irradiating the liquid. A second photo detector is configured to generate a second electric signal, which is indicative of an amount of a second spectrum of light irradiating the liquid, where the second spectrum is not equal to the first spectrum. A circuit combines the first and second signals to generate an output signal, which indicates an amount of a range of ultraviolet light irradiating the liquid.

BRIEF DESCRIPTION OF THE DRAWINGS

These and other aspects of the present invention will become readily apparent to those skilled in the art from the following detailed description of the preferred embodiments and from the attached figures, which are meant to illustrate and not to limit the invention, and wherein.

DETAILED DESCRIPTION OF THE PREFERRED EMBODIMENT

While illustrated in the context of a UV water disinfector, it will be understood that the UV detector of the preferred embodiments will have application in a variety of contexts.

Figure 1:
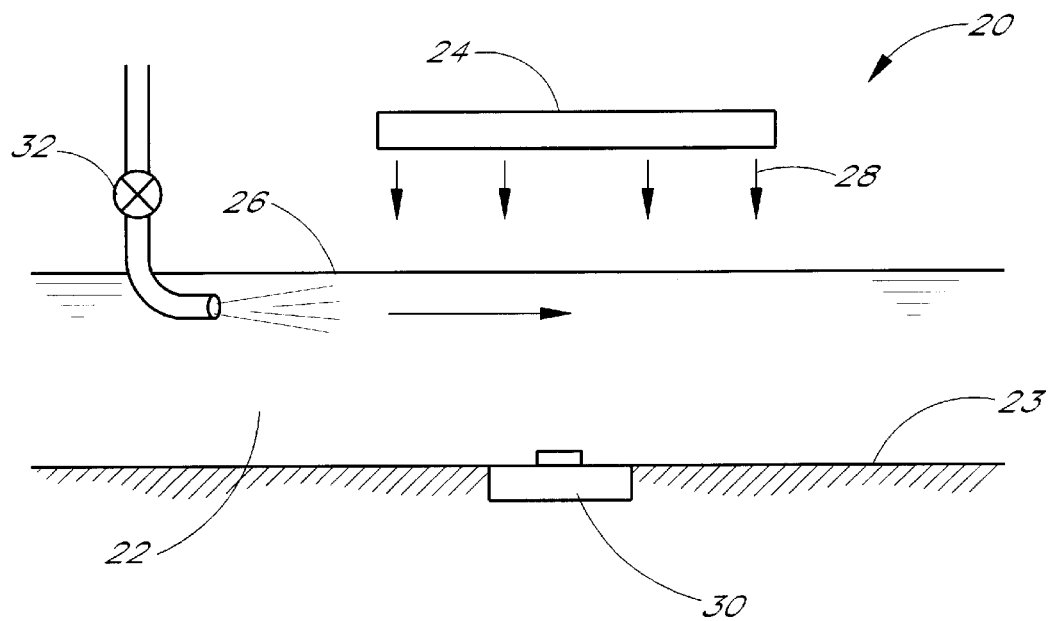
FIG. 1 is a schematic sectional side view of a disinfection channel of a UV liquid disinfector constructed in accordance with a preferred embodiment of the present invention.

FIG. 1 shows a disinfection channel 20 of a UV water disinfector having features according to the teachings of the present invention. The disinfector is designed to disinfect a liquid such as water 22. The water 22 is directed to flow through the channel 20 as shown. Preferably, a solenoid valve 32 is configured to selectively control the flow of water 22 into the disinfection channel 20. During normal operation, the valve 32 remains open so that water 22 may enter channel 20. The valve 32 may be closed, however, to completely restrict the flow and effectively shut off the entire disinfection unit.

A lamp 24 is provided above the surface 26 of the water 22, in the manner disclosed by U.S. Pat. No. 5,780,860 to Gadgil et al., incorporated herein by reference. The lamp 24 emits radiant light onto the water 22, as indicated by arrows 28. A portion of the radiant light emitted is UV light, which is absorbed by and disinfects the water 22. The flowrate of the water 22 is preferably maintained at a constant level, and is low enough so that the water 22 can absorb sufficient UV energy to be completely disinfected. The flow may be gravity driven or may be controlled by a system of pumps, as desired. For optimal disinfection, the water flow is substantially laminar, and baffles and weirs, as taught by Gadgil '860, can be employed for this purpose. After flowing through the disinfection channel 20, the completely disinfected water 22 exits the disinfection unit.

As shown in FIG. 1, a UV light sensor assembly 30 may be secured underneath the floor 23 of the disinfection channel 20. A top light-receiving portion of the sensor assembly 30 extends through a hole in the floor 23 and protrudes above the floor surface into the water flowstream. Sensor assembly 30 monitors the intensity of the UV portion of radiant light 28 passing through the water 22 and generates an output current or, more preferably, an output voltage that is proportional to the UV light intensity. In the preferred embodiment, because the measured light has passed through the water 22 before reaching the sensor 30, the turbidity of the water 22 is accounted for when measuring the UV dosage received by the water.

Thus, in the illustrated embodiment, the sensor 30 is submerged within the water 22, while the lamp 24 is suspended above the water 22. It will be understood, however, that the preferred sensor 30 will have utility in a variety of other types of UV disinfectors. For example, the UV lamp is often submerged within the flowing water to effectively employ light radiating in all directions from the lamp for disinfection.

The UV disinfection unit may be electronically configured by means well known in the electronic arts to trigger events within the system. In the preferred embodiment, an electronic control system controls the UV disinfection unit according to the UV light exposed to the water. In particular, the control system shuts the system off if the sensor assembly 30 detects insufficient intensity of UV light, and turns the system back on if the UV light intensity rises back to a comfortable level. For example, whenever the output current or voltage is too low, which might occur if the power to the lamp 24 drops or cuts out, or if the lamp bulb fuses, the solenoid valve 32 can be closed to block the flow of water 22 into the disinfection channel, effectively shutting off the system. An alarm can be activated to alert system attendants, in addition to or in place of system shut down.

Accordingly, the control system of the UV disinfection unit, discussed in greater detail below, is preferably configured to electronically trigger a safety mechanism, such as by closing the solenoid valve 32 and/or activating an alarm if the output current or voltage drops below a first predetermined amount. This first predetermined amount represents a level of current or voltage corresponding to a UV intensity cutoff, below which there is a danger that the water 22 will not be successfully disinfected. Thereafter, should the output current or voltage rise above a second predetermined amount, representing a level of current or voltage corresponding to a UV light intensity above which it is safe to resume disinfection, the control system will preferably automatically open the solenoid valve 32 to reinitiate disinfection. In other arrangements, the disinfection system can be configured to be manually reinitiated. The second predetermined amount is preferably greater than or equal to the first predetermined amount, to ensure that the disinfection system will not be reinitiated if there is still a danger of ineffective disinfection.

One method of detecting the UV light exposed to the water 22 is to use a single solid state detector chip in combination with a UV bandpass filter. The chip generates a photo-induced current proportional to the intensity of the light to which it is exposed. The UV bandpass filter screens out all light wavelengths outside of the desired UV spectrum, so that the photo-induced current is proportional to the amount of UV light. The output current can be used to control elements within the disinfection system, as described in more detail below.

More preferably, two solid state silicon photodetector chips are electrically connected in reverse parallel to generate an electric current proportional to the UV light. In the preferred configuration of the present invention, the UV light sensor assembly 30 includes two solid state silicon photodetector chips 34 and 36.

Figure 2:
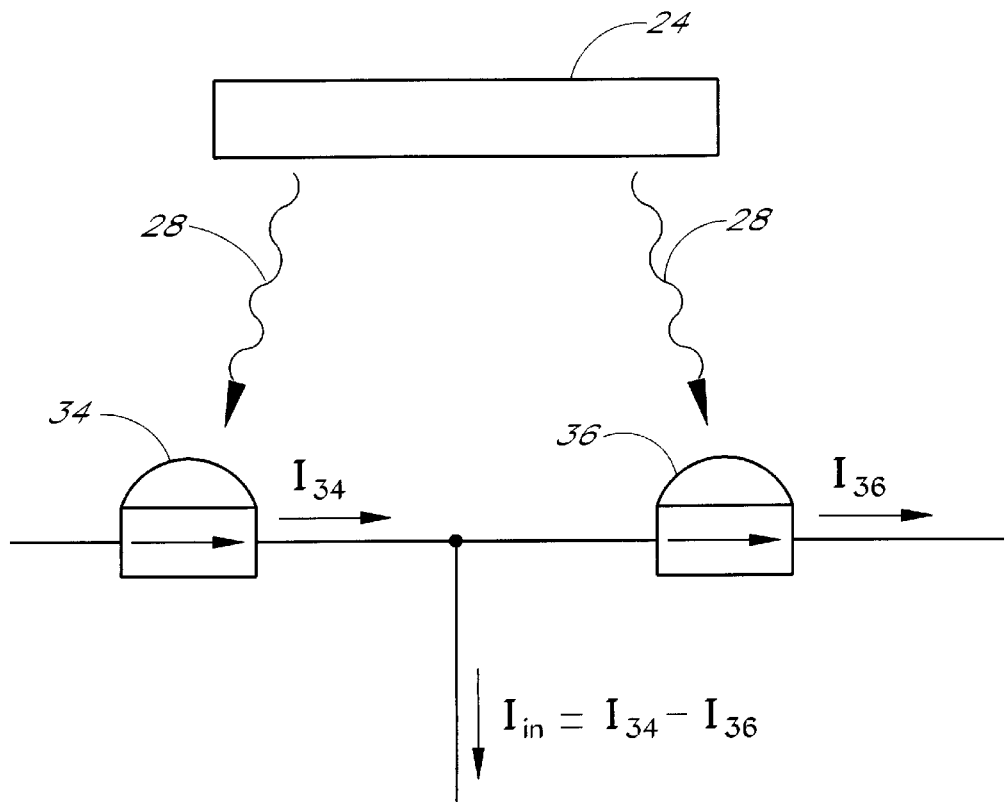
FIG. 2 schematically illustrates a UV light detection system for the embodiment of FIG. 1, utilizing a pair of photodetector chips.

FIG. 2 illustrates a preferred manner of using the chips 34 and 36. The first chip 34 is sensitive to and generates an output current $I_{34}$ proportional to the amount of visible, infra-red, and UV light detected. In contrast, the second chip 36 is sensitive to substantially the same spectrum, with the exception of UV light, and generates an output current $I_{36}$ proportional to the amount of visible and infra-red light detected. Therefore, when the two chips are exposed to radiant light 28 emitted from the lamp 24, the difference between their output currents, $I_{34}-I_{36}$, is approximately proportional to the amount of UV light to which the chips are exposed. According to the present invention, chips 34 and 36 are electrically connected in reverse parallel so that their output currents tend to cancel. The resulting current $I_{in}$ is the difference between the output currents of each chip, which, as explained, is proportional to the UV light intensity.

Figure 5:
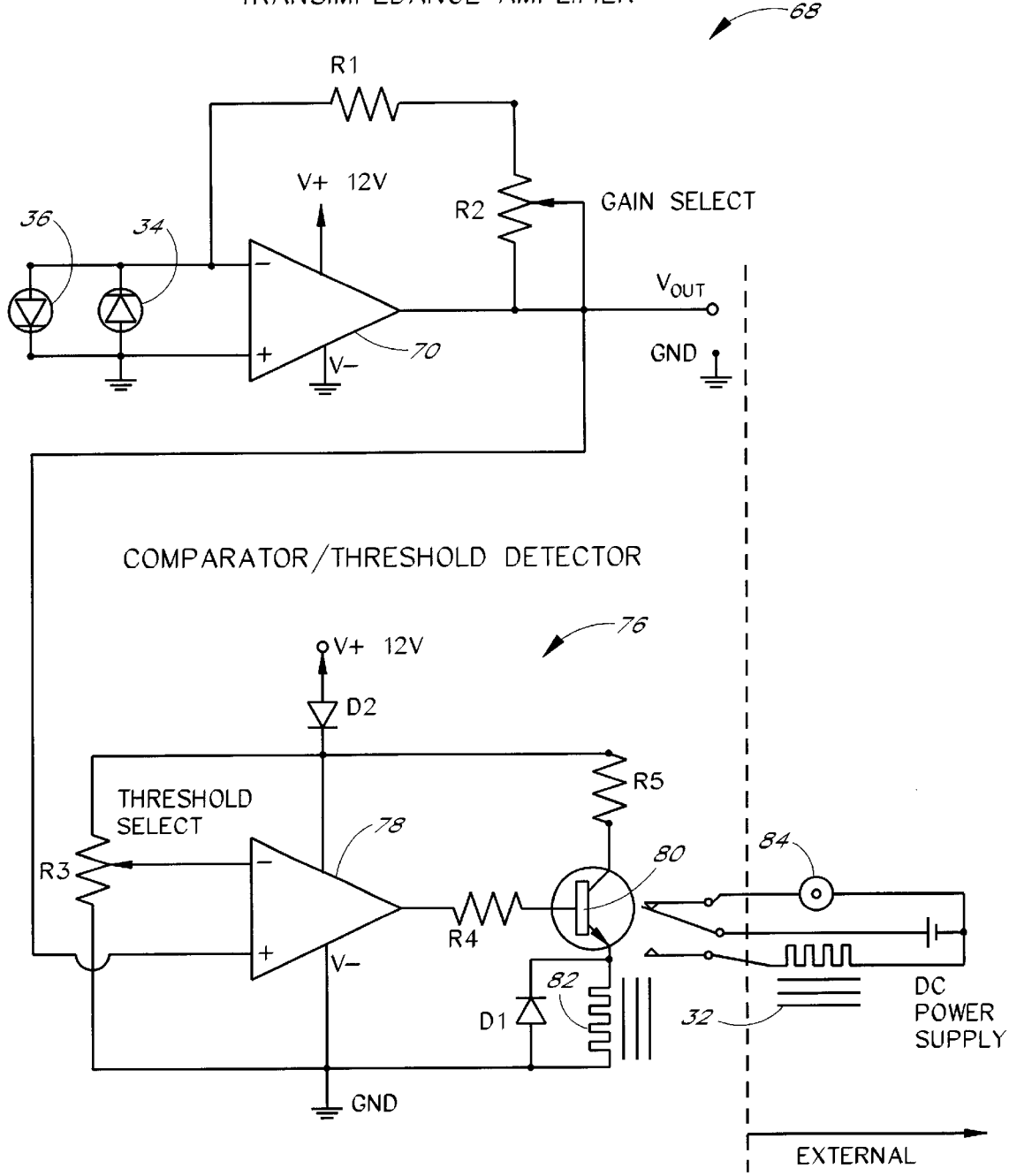
FIG. 5 is a circuit diagram illustrating a preferred electrical configuration of a UV light detection and control system having features and advantages in accordance with the teachings of the present invention.

As discussed in more detail with respect to FIG. 5, the input current $I_{in}$ is amplified and converted by suitable means, such as a transimpedance amplifier, to an output voltage $V_{out}$, which is also proportional to the UV light intensity. In this way, the sensor assembly 30, comprising detector chips 34 and 36 and an amplifier, is insensitive to visible and infra-red wavelengths even though each detector chip is sensitive thereto. Furthermore, a quad (or 4x) operational amplifier may be included to allow for additional signal conditioning circuitry, such as a comparator and threshold detector, so that the output voltage signal $V_{out}$ can be used to control a solenoid valve 32 and/or an alarm in the UV liquid disinfector, discussed in greater detail below.

There are several advantages of this dual photodetector method of detecting UV light, including low cost, long lifespan (typically greater than five years), enhanced optical and mechanical stability, and low output signal "noise." The total cost of UV sensor assembly 30 is considerably reduced compared to vacuum photodiode technology. Sensor assembly 30 uses "off the shelf" detector chips and optics, is easy to implement, and is at least equally robust, with respect to mechanical shock and humidity, as most varieties of the lamp 24.

Furthermore, the output voltage generated by sensor assembly 30 exhibits less noise than prior art detection systems. This is because a large portion of the noise generated by each of the chips 34 and 36 becomes cancelled out as the two signals are subtracted. Such noise includes current generated by the detection of electromagnetic energy emitted from other components within the UV water disinfector, such as from power lines, the lamp ballast, etc. Since both chips detect almost the same amount of noise, most of the noise is cancelled when the currents $I_{34}$ and $I_{36}$ are opposed, as shown in FIG. 2. Optionally, electrical shielding can be employed to further reduce such noise.

The preferred dual detector sensor also exhibits advantages over the single solid state detector approach described above. One advantage is that it is less expensive. In the single detector method, the UV bandpass filter alone can cost more than the entire sensor assembly 30. Another advantage is that the signal generated by the dual detector sensor generally contains less noise detected from other components within the UV water disinfector, for the same reasons mentioned above.

Hamamatsu Corporation of New Jersey, U.S.A., sells P-N junction silicon detector chips suitable for the purposes of the present invention. According to a preferred embodiment of the invention, Hamamatsu Detectors S1226-18BQ and S1226-18BK are used as detector chips 34 and 36, respectively. These detectors generate current at the rate of about 0.1 amps per watt of light detected (0.1 A/W). Also, these detectors are identical in every respect except for the window material that protects the chip, which is housed in a separate hermetically sealed TO-18 metal can. Hamamatsu Detector S1226-18BQ photodetector 34) includes an integral quartz window that transmits visible, near infra-red, and UV wavelengths. Since quartz does not transmit significantly below 190 nm, this chip is sensitive to wavelengths above 190 nm. In contrast, Hamamatsu Detector S1226-18BK (photodetector 36) has a borosilicate window that transmits wavelengths within the range of about 190 nm–310 nm, i.e., visible and infra-red wavelengths.

Those in the art will understand that the use of Hamamatsu detectors according to the above-described preferred embodiment is exemplary and not limiting. Any two detectors that exhibit the desired property of generating photo-induced currents whose difference is proportional to the intensity of a desired spectrum of light may be utilized without departing from the spirit and scope of this invention. Thus, a suitable first detector generates a photo-induced current proportional to the intensity of light detected within a first spectrum, including a desired range of UV light. A suitable second detector generates a photo-induced current proportional to the intensity of light detected within a second spectrum, substantially the same as the first spectrum but excluding the desired range of UV light. Also, it will be readily apparent to those skilled in the art that the output voltage $V_{out}$, and consequently the advantages of the present invention, can alternatively be obtained by separately converting each of the currents $I_{34}$ and $I_{36}$ into voltage signals, via current-to-voltage converters, and taking the difference between the separate voltage signals. Current-to-voltage conversion is well-known in the art.

Figure 3:
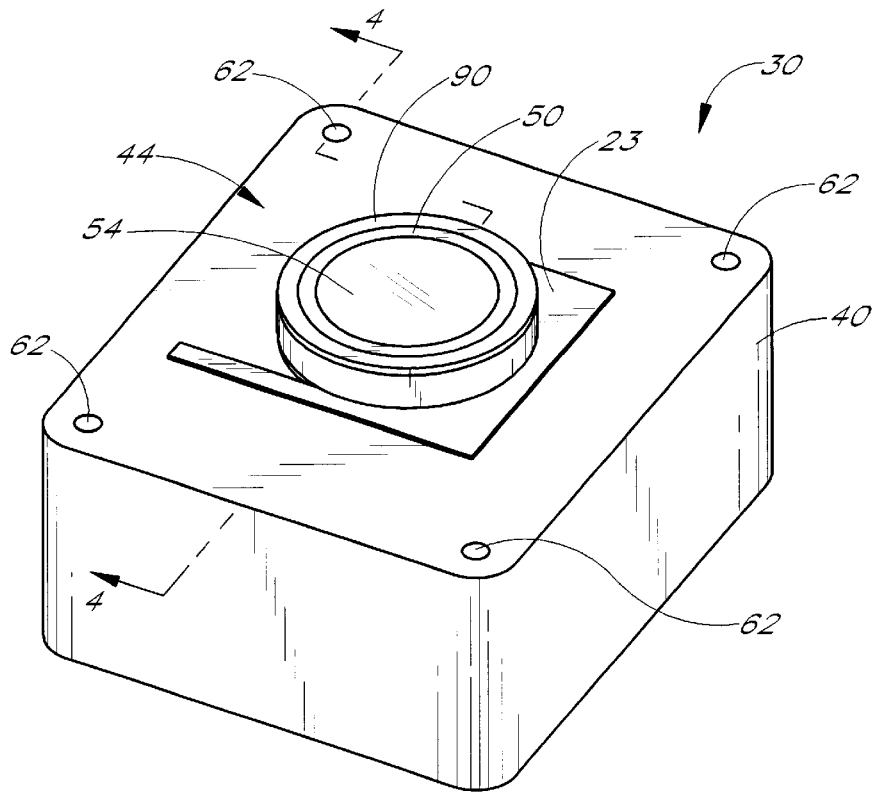
FIG. 3 is a perspective view of a UV light sensor assembly for the embodiment of FIG. 1.
Figure 4:
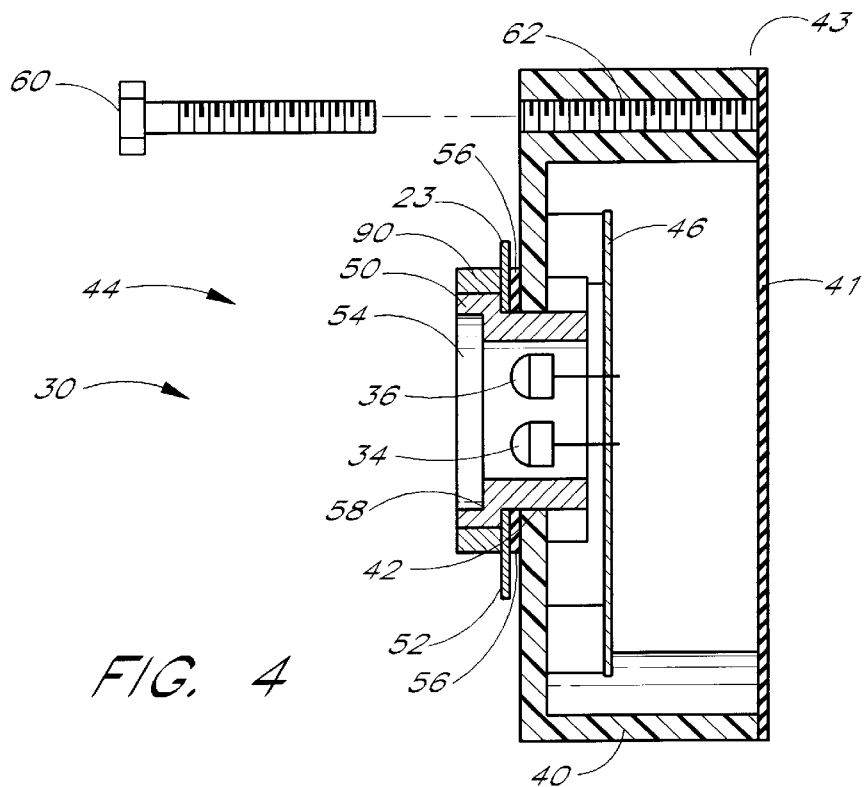
FIG. 4 is a sectional view of the UV light sensor assembly, taken along lines 4—4 of FIG. 3.

FIGS. 3 and 4 illustrate a preferred configuration of the UV light sensor assembly 30 of the present invention. Preferably, only the top portion of the sensor assembly 30 extends above the floor 23. The illustrated sensor assembly 30 comprises a small hollow plastic box 40, a detector chip housing 44, a circuit board 46, and a lower plate 41 attached to the bottom of box 40. A preferred size of the box 40 is about 3 cm×5 cm×1 cm. The housing 44 comprises a cylindrical fitting 50, a window 54, and the detector chips 34 and 36. The upper end of fitting 50 has a larger diameter than the lower end thereof The lower end of fitting 50 is adapted to be tightly received in sealed fashion within a hole in the floor 23 of the disinfection channel 20 (see FIG. 1). The box 40 has a circular opening 42 which is also adapted to receive in sealed fashion the lower end of fitting 50. The fitting 50 can be rigidly secured to the box 40 by any of a variety of means, such as adhesives or nut and bolt combinations, giving due consideration to the goals of strength, stability, rigidity, water-tightness, etc. A silicon rubber O-ring seal 56 is provided between the top of the box 40 and the floor 23 of the disinfection unit water tray. Preferably, the top of the fitting 50 is externally threaded to receive a nut 90 screwed thereon to fasten the housing 44 onto the floor 23. Optionally, bolts 60 may be provided within vertical channels 62 in the box 40, to secure the sensor assembly 30 to the floor 23. Although only a top portion of the sensor assembly 30 is shown above the floor 23 in FIGS. 1, 3, and 4, those in the art will understand that the entire assembly, including the box 40, could be secured above the floor 23 without departing from the spirit and scope of this invention.

The fitting 50 includes an annular ledge 58 at its upper end, within which the window 54 fits tightly within. Preferably, the junction between the fitting 50 and the window 54 is water-tight to prevent water 22 from entering into the sensor assembly 30. This can be achieved by providing a Viton O-ring seal between the window 54 and walls of the fitting 50. Optionally, a ring-shaped plate can also be provided between the Viton seal and the window 54, to compress the seal in order to produce a more effective water-tight seal. Detector chips 34 and 36 are positionally fixed underneath the window 54 and electrically connected to the circuit board 46. Any suitable means of support for the chips 34 and 36 may be utilized, such as a horizontal support disk within the lower end of fitting 50 or a plurality of vertical supports extending upward from the circuit board 46. Likewise, the circuit board 46 may be supported by any of a variety of means, such as by an attachment to fitting 50 or by vertical supports extending from the lower plate 41. Alternatively, the circuit board may be directly secured to the plate 41. In still other arrangements, the circuit board can be positioned outside the sensor box 40, and wires can carry signals outside the box to the circuit board. Such an arrangement is particularly advantageous for centrally locating circuitry for the entire disinfection unit.

The detector chips 34 and 36 are oriented in a manner such that they detect light 28 emitted from the lamp 24 and passing through the window 54 of the UV sensor assembly 30. In other words, the windows of the chips 34 and 36 directly face the bottom of window 54. In general, the window 54 may be formed from any substance that transmits a spectrum including the UV range of interest. It is not necessary that the window 54 filter any wavelengths of light, although filtering low spectrum (e.g., infrared) light would not adversely affect the sensor 30. In the preferred embodiment, window 54 is formed from quartz. Quartz does not transmit wavelengths below 190 nm, and Hamamatsu Detector S1226-18BQ (photodetector 34) also has a quartz window of its own, limiting the detection system to wavelengths above 190 nm in any case. Thus, a quartz window 54 does not affect the response of the UV sensor assembly 30. Under extreme conditions, dust or sediment on the window 54 or detector chips 34 and 36 could conceivably give a false indication of the UV light. This problem can be eliminated by using a spatial averager or diffuser. A suitable method is to use sandblasted quartz as the window 54.

FIG. 5 is a circuit diagram of a preferred electrical configuration of the UV light detection and control system of the present invention, comprising circuits 68 and 76.

Circuit 68 is configured to monitor the level of UV light exposed to the UV light sensor assembly 30, and includes a standard transimpedance amplifier that generates an output voltage $V_{out}$ proportional to the amount of UV light detected. The voltage of an external power supply (e.g., a 9V battery) is made available to the output pins proportionally to the current at the inverting (−) and non-inverting (+) input pins of an operational amplifier 70. The sensor assembly 30 generates an input photocurrent $I_{in}=I_{34}-I_{36}$. Feedback resistors R1 and R2 (preferably a variable resistor) determine the gain or magnification factor and relate the output voltage $V_{out}$ to the input photocurrent $I_{in}$ via the relation $V_{out}=(R1+R2)I_{in}$.

The circuit preferably operates on a single power supply rather than the more typical split or double power supply. This reduces the cost of the detection system and allows for the circuit ground to be connected to the negative voltage supply pin of the operational amplifier 70. The output voltage $V_{out}$ is then between 0 and +9V (if a 9V battery is used as the power supply) if the negative cathode of chip 34 (N type layer of Hamamatsu Detector S1226-18BQ) is connected to the inverting (−) input of operational amplifier 70. The circuit can be run off an independent battery (i.e., 9V) or off a power supply connected to the line voltage if proper grounding, isolation, and shielding is observed. Alternatively, the battery may also be charged by a power supply.

As mentioned above, the output signal $V_{out}$ from the transimpedance amplifier is preferably used to control a solenoid valve 32 and/or an alarm 84 based on the amount of UV light detected. As shown in FIG. 5, a second circuit 76 is cascaded and linked to the output of circuit 68. An operational amplifier 78 is used to create a comparator and threshold detector that controls an output transistor 80 and a relay 82. A potentiometer sets the voltage to which the operational amplifier 78 responds. The operational amplifier 78 is set at unity gain and drives the relay 82 via the transistor 80 when the voltage rises above a pre-set value. The relay 82 controls the solenoid valve 32 and/or the alarm 84 connected to the normally open or normally closed relay contacts. The AC line voltage (110 V or 220 V) is connected in series with the solenoid valve 32 and/or the alarm 84 via the relay 82. Alternatively, an SCR or optocoupler can also be used at the output of the operational amplifier 78 as an interface between the comparator and the solenoid valve 32. A low power DC alarm 84 can also be connected in series with the output of the transistor 80. Depending on the desired logic of the control system of the UV disinfection unit, the wiper of the potentiometer can be placed at the inverting (−) or non-inverting (+) inputs of the operational amplifier 78, and the normally open or normally closed contact points of relay 82 can be utilized. Preferably, the valve 32 automatically shuts, effectively shutting off the disinfection unit, when the amount of UV light detected drops dangerously close to the level below which disinfection is unsuccessful. Alternatively, the system may be configured to sound the alarm 84, signalling a dangerously low level of UV light.

The following table lists some preferred component types and ratings for the components illustrated in the circuits 68 and 76 of FIG. 5:

| Symbol | Component | Type/Rating |
| --- | --- | --- |
| 34 | Photodetector | Hamamatsu S1226-18BQ |
| 36 | Photodetector | Hamamatsu S1226-18BK |
| 70 | Operational Amplifier | ¼ LM324N |
| 78 | Operational Amplifier | ¼ LM324N |
| R1 | Resistor | 1 kΩ |
| R2 | Resistor | 2 MΩ, B1 72 PR 2 MΩ |
| R3 | Resistor | 2 MΩ, B1 72 PR 2 MΩ |
| R4 | Resistor | 1 kΩ |
| R5 | Resistor | 200 kΩ |
| D1 | Diode | 1N914 |
| D2 | Diode | 1N914 |
| 80 | Transistor | 2N2222A |
| 82 | Relay | Aromat RSD-5V |
| 84 | Alarm | Piezo Buzzer |
| 32 | Solenoid Valve | DC 12 V |

In the illustrated embodiment, the electrical circuitry of FIG. 5 is enclosed within the box 40 of the UV light sensor assembly 30. This limits the possibility of signal degradation and prevents interference from other electromagnetic sources that might occur if the circuit 68 and 76 were located outside of the disinfection channel. However, the sensor assembly 30 could house only the detector chips 34 and 36, in which case the remainder of the electrical circuits 68 and 76 would be located outside of the disinfection channel 20.

Although this invention has been disclosed in the context of certain preferred embodiments and examples, it will be understood by those skilled in the art that the present invention extends beyond the specifically disclosed embodiments to other alternative embodiments and/or uses of the invention. Thus, it is intended that the scope of the present invention herein disclosed is not limited to the particular disclosed embodiments described above, but should be determined only by a fair reading of the claims that follow.

I claim:

1. An ultraviolet light detector for detecting a level of ultraviolet light exposed to a liquid flowing within an ultraviolet liquid disinfection unit, said detector comprising:
    a first photodetector configured to generate a first electric signal proportional to a level of light received by the detector and within a first spectrum of wavelengths, said first spectrum including ultraviolet light;
    a second photodetector configured to generate a second electric signal proportional to a level of light received by the detector and within a second spectrum of wavelengths, said second spectrum substantially including said first spectrum except for a range of ultraviolet light; and
    circuitry connecting said first and second electric signals to generate an output electric signal proportional to a level of light received by the detector and within the range of ultraviolet light.

2. The ultraviolet light detector according to claim 1, wherein said circuitry connects said first and second electric signals in reverse parallel.

3. The ultraviolet light detector according to claim 1, wherein said first, second and output electric signals comprise currents, further comprising a transimpedance amplifier circuit configured to convert said output electric current into an output voltage.

4. The ultraviolet light detector according to claim 1, further comprising a comparator circuit configured to close a solenoid valve within said ultraviolet liquid disinfection unit if said output electric signal is lower than a first predetermined amount, said solenoid valve configured to control a flow of said liquid through said disinfection unit.

5. The ultraviolet light detector according to claim 4, wherein said comparator circuit is configured to open and maintain in an open position said solenoid valve if said output electric signal is greater than a second predetermined amount, said second predetermined amount being greater than or equal to said first predetermined amount.

6. The ultraviolet light detector according to claim 1, further comprising a comparator circuit configured to activate an alarm if said output electric signal is lower than a predetermined amount.

7. The ultraviolet light detector according to claim 1, wherein said disinfection unit comprises a UV lamp suspended above said liquid.

8. The ultraviolet light detector according to claim 1, wherein said detector is submerged within said liquid.

9. The ultraviolet detector according to claim 1, wherein said second photodetector comprises a borosilicate window.

10. The ultraviolet light detector according to claim 1, wherein said first and second photodetectors comprise solid state silicon photodetector chips.

11. The ultraviolet light detector according to claim 1, wherein said first photodetector is sensitive to visible, infrared, and ultraviolet light, and said second photodetector is sensitive to visible and infrared light.

12. An ultraviolet light detector according to claim 11, wherein said first photodetector is sensitive to wavelengths of light greater than or equal to approximately 190 nm, and said second photodetector is sensitive to wavelengths of light less than or equal to approximately 310 nm.

13. A method of detecting a level of ultraviolet light received at a detector, comprising:
    generating a first photo-induced electric signal related to an intensity of light in a first spectrum of wavelengths, said first spectrum including a desired range of ultraviolet light;
    generating a second photo-induced electric signal related to an intensity of light in a second spectrum of wavelengths, the second spectrum substantially including the first spectrum and substantially excluding the desired range of ultraviolet light; and
    subtracting said second electric signal from said first electric signal to generate an output electric signal related to the level of ultraviolet light received at the detector.

14. An ultraviolet detector comprising:
    a detection region;
    a first solid state photodetector configured to generate a first electric current proportional to a level of radiant light received at the detection region within a first range of light wavelengths, said first range including a desired range of ultraviolet light wavelengths; and
    a second solid state photodetector configured to generate a second electric current proportional to a level of radiant light received at the detection region within a second range of light wavelengths, said second range substantially including the first range of light wavelengths except for the desired range of ultraviolet light wavelengths;
    wherein said first and second electric currents are connected in reverse parallel to generate an output electric current proportional to a level of light within the desired range of ultraviolet light wavelengths received at the detection region.

* * * * *